United States Patent
Mazzocchi et al.

(10) Patent No.: US 6,793,664 B2
(45) Date of Patent: Sep. 21, 2004

(54) SYSTEM AND METHOD OF MINIMALLY-INVASIVE EXOVASCULAR ANEURYSM TREATMENT

(75) Inventors: Rudy A. Mazzocchi, Indian Harbor Beach, FL (US); Thomas I. Miller, Palm Bay, FL (US); Kari Parmer, Melbourne, FL (US); Timothy Alan Parmer, Melbourne, FL (US); Matthew S. Solar, Indialantic, FL (US)

(73) Assignee: Image-Guided Neurologics, Melbourne, FL (US)

( * ) Notice: Subject to any disclaimer, the term of this patent is extended or adjusted under 35 U.S.C. 154(b) by 7 days.

(21) Appl. No.: 09/884,434

(22) Filed: Jun. 19, 2001

(65) Prior Publication Data

US 2002/0022837 A1 Feb. 21, 2002

Related U.S. Application Data

(60) Provisional application No. 60/212,420, filed on Jun. 19, 2000.

(51) Int. Cl.[7] .............................................. A61B 17/08
(52) U.S. Cl. ...................................... 606/157; 606/158
(58) Field of Search ........................... 6/157, 158, 130; 600/411, 425

(56) References Cited

U.S. PATENT DOCUMENTS

| 535,798 A | 3/1895 | Hawkes |
| 1,352,978 A | 9/1920 | Lantieri et al. |
| 3,326,217 A | 6/1967 | Kerr |
| 3,518,993 A | 7/1970 | Blake |
| 4,024,868 A | 5/1977 | Williams |
| 4,386,602 A * | 6/1983 | Sheldon et al. ............ 606/130 |
| 4,440,170 A | 4/1984 | Golden et al. |
| 4,478,219 A | 10/1984 | Rozario et al. |
| 4,527,562 A | 7/1985 | Mericle |
| 4,681,107 A | 7/1987 | Kees, Jr. |
| 4,706,668 A | 11/1987 | Backer ....................... 128/325 |
| 4,943,298 A | 7/1990 | Fujita et al. |
| 4,966,603 A | 10/1990 | Focelle et al. |
| 5,174,276 A | 12/1992 | Crockard ....................... 128/4 |
| 5,201,746 A | 4/1993 | Shichman |
| 5,201,900 A | 4/1993 | Nardella ..................... 606/157 |
| 5,234,449 A | 8/1993 | Bruker et al. |
| 5,304,188 A | 4/1994 | Marogil |
| 5,354,306 A | 10/1994 | Garvey, III et al. |
| 5,520,701 A | 5/1996 | Lerch |

(List continued on next page.)

FOREIGN PATENT DOCUMENTS

| EP | 0178469 | 4/1986 | ........... A61B/17/12 |
| EP | 0326426 | 8/1989 | ........... B29C/61/00 |
| EP | 0630615 | 7/1998 | ........... A61B/17/12 |
| WO | 00/19927 | 4/2000 | ........... A61B/19/00 |

OTHER PUBLICATIONS

Goodwin, S., "New Stroke Treatment: 'Aneurysm Coil' Available to Patients With Inoperable Aneurysms", http://www.emory.edu/WHSC/HSNEWS/archives/mar96/aneurysm.html, 2 p., (Mar. 25, 1996).

(List continued on next page.)

Primary Examiner—Michael Peffley
(74) Attorney, Agent, or Firm—Schwegman, Lundberg, Woessner & Kluth, P.A.

(57) ABSTRACT

This document discusses an exovascular approach to treating an aneurysm using a minimally-invasive instrument guided by magnetic resonance imaging (MRI), computed tomography (CT), or another suitable imaging device. A trajectory guide entry device assists in targeting the aneurysm and determining the proper trajectory thereto. Examples of the aneurysm treatment device include a clip, a clasp, a snare, a loop, a hook, a staple, and an electrocautery or other electrode, or any combination of such devices. The aneurysm treatment device is delivered by a probe, such as a tube or other catheter.

52 Claims, 12 Drawing Sheets

U.S. PATENT DOCUMENTS

| | | | | |
|---|---|---|---|---|
| 5,569,274 A | | 10/1996 | Rapacki et al. | 606/158 |
| 5,634,932 A | * | 6/1997 | Schmidt | 606/157 |
| 5,916,235 A | | 6/1999 | Guglielmi | 606/200 |
| 5,928,226 A | | 7/1999 | Guglielmi et al. | 606/32 |
| 5,941,888 A | | 8/1999 | Wallace et al. | 606/108 |
| 5,972,003 A | * | 10/1999 | Rousseau et al. | 606/151 |
| 6,019,724 A | | 2/2000 | Gronningsaeter et al. | 600/439 |
| 6,024,695 A | | 2/2000 | Taylor et al. | 600/102 |
| 6,195,577 B1 | | 2/2001 | Truwit et al. | 600/411 |
| 6,272,370 B1 | * | 8/2001 | Gillies et al. | 606/130 |
| 6,464,710 B1 | * | 10/2002 | Foster | 606/158 |

OTHER PUBLICATIONS

Kaut–Roth, C., "MRI Safety", http://www.t2star.com/safety_1/safety1.html, pp. 1–11, (Nov. 1996).

Martin, J.L., "Vascular Malformations of the CNS: Cerebral Aneurysms", *Surgery, the Medicine Group, Ltd., Arlington GB*, 13 (6), pp. 133–136, (Jun. 1, 1995).

Sundt, T.M., "Chapter 6: Basic Principles and Technques", *In: Surgical Techniques for Saccular & Giant Intracranial Aneurysms*, Williams & Wilkins, pp. 39–56, (1990).

* cited by examiner (A)  CLIP CLOSED AND RETRACTED (B)  CLIP OPEN AND EXTENDED (C)  CLIP CLOSED AROUND ANEURYSM (D)  RETAINER OPENED TO RELEASE CLIP

SYSTEM AND METHOD OF MINIMALLY-INVASIVE EXOVASCULAR ANEURYSM TREATMENT

CROSS-REFERENCE TO RELATED APPLICATION

This patent application claims the benefit of priority, under 35 U.S.C. Section 119(e), to U.S. Provisional Patent Application Ser. No. 60/212,420, entitled "METHOD OF MINIMALLY-INVASIVE ANEURYSM CLIPPING AND APPARATUS," filed Jun. 19, 2000, the disclosure of which is incorporated herein by reference in its entirety.

TECHNICAL FIELD

This document relates generally to minimally-invasive surgical systems, devices, and methods, and particularly, but not by way of limitation, to a system and method of minimally-invasive exovascular aneurysm treatment.

BACKGROUND

An aneurysm is an abnormal dilatation of a blood vessel. Brain aneurysms pose a particular risk of rupture and resulting hemorrhage, resulting in possible significant loss of brain function and even death. Autopsy studies have estimated that between about 1.5% and 8% of the population have intracranial aneurysms. Between 60,000 and 80,000 cerebral aneurysms are diagnosed annually in the U.S. Of these patients, about 20,000 to 30,000 are diagnosed following the occurrence of subarachnoid hemorrhage. The annual risk of an aneurysmal rupture is about 2%. Patients that experience aneurysmal rupture typically experience a mortality rate of about 50–60%. If the ruptured aneurysm is left untreated, about 25–35% of such patients will die of recurrent hemorrhage. For about 20–40% of those patients that do survive, the ruptured aneurysm results in a significant deficit in neurological function.

One conventional technique for treating a brain aneurysm uses standard open surgical intervention techniques. A craniotomy is performed to create a relatively large opening in the patient's skull. The surgeon uses conventional surgical instruments to retract intervening brain tissue to expose the blood vessel at the aneurysm for direct visualization. With the aneurysm and associated blood vessel in view, the surgeon manipulates and treats the aneurysm using traditional surgical instruments to clip or staple either the body of the vessel or the neck of the aneurysm. Although such surgical clipping yields a high likelihood of procedural success, it is highly invasive. Therefore, it risks inducing associated brain trauma, thereby requiring a long recovery time. Moreover, a significant number of brain aneurysms are located very deep in the brain, rendering such conventional surgical techniques difficult.

Another technique for treating a brain aneurysm uses an endovascular approach. For example, a catheter may be introduced (e.g., near a subject's groin) through a blood vessel and advanced to the aneurysm. In one technique, a detachable coil is introduced through the endovascular catheter and "packed" into the interior of the aneurysm. This coil, which is usually constructed of stainless steel and/or platinum wire, is intended to interrupt the turbulent blood flow into the aneurysm. The resulting blood clots within the interior of the aneurysm. This reduces the risk of aneurysmal rupture. Another endovascular method of treating aneurysms uses a detachable balloon. The balloon is inflated with cyanoacrylates to occlude the interior of the aneurysm. Yet another endovascular method of treating aneurysms introduces an intravascular stent or graft that occludes the adjacent neck of an aneurysm sufficiently to interrupt blood flow into the aneurysm while maintaining continued flow through the native vessel.

These endovascular techniques for treating aneurysms, however, have not exhibited as high a likelihood of success as the open surgery techniques discussed above. Moreover, application of the endovascular techniques is generally limited to non-bifurcating, small-neck aneurysms, which actually constitute a small percentage of the clinically-diagnosed aneurysms. Furthermore, some aneurysms are exceedingly difficult to reach endovascularly because they require traversal of a long tortuous path through the accessing vessels. For these and other reasons, the present inventors have recognized a need for improved techniques and associated devices for accessing and treating brain or other aneurysms.

SUMMARY

In contrast to the above-discussed open surgery and endovascular approaches to treating aneurysms, this document discusses a minimally-invasive exovascular approach to treating an aneurysm. Using such a minimally-invasive technique, the surgeon need only make a small opening for inserting an exovascular instrument to the aneurysm. In order to perform the treatment, the surgeon need not visualize the aneurysm directly. Instead, a magnetic resonance imaging (MRI), computed tomography (CT), or other suitable imaging device is provided to allow the surgeon to exovascularly guide a minimally-invasive aneurysm treatment device through the brain to the aneurysm, apply the treatment device to the desired portion of the aneurysm, and then remove the aneurysm treatment device. In a further example, an image-guided entry device is used to provide more accurate targeting and determination of a trajectory from the minimally-invasive entry opening to the aneurysm to be treated. The minimally-invasive techniques discussed in this document may permit more effective treatment of aneurysms that would be difficult to access or treat using endovascular techniques. Moreover, these minimally-invasive techniques may result in less shifting of brain tissue than open surgery techniques. This may permit more accurate targeting of the aneurysm, and less trauma to the intervening brain tissue.

In one example, this document discusses a system that includes an elongate exovascular probe. The probe includes proximal and distal ends. The probe also includes an outer dimension that is less than about 18 millimeters to permit the probe to be introduced through a similarly-sized minimally-invasive opening in a portion of a subject's skull and exovascularly advanced to an aneurysm within the skull. The system also includes an aneurysm treatment device carried by the probe. The aneurysm treatment device is dimensioned to permit the aneurysm treatment device to be introduced through the opening.

In another example, this document discusses a method of aneurysm treatment. The method includes forming an opening in a subject's skull. The opening having a diameter that is less than or equal to the diameter of a burr hole. A probe is exovascularly inserted through the opening to an aneurysm using real-time or preoperative imaging to guide the probe to the aneurysm. An aneurysm treatment device is exovascularly introduced through a lumen in the probe to the aneurysm. Using the aneurysm treatment device, a morphology of the aneurysm is altered. Other aspects of the invention will be apparent on reading the following detailed description of the invention and viewing the drawings that form a part thereof.

BRIEF DESCRIPTION OF THE DRAWINGS

In the drawings, which are offered by way of example, and not by way of limitation, and which are not necessarily drawn to scale, like numerals describe substantially similar components throughout the several views. Like numerals having different letter suffixes represent different instances of substantially similar components.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents.

In this document, the term "minimally-invasive" shall be interpreted as referring to techniques that are less invasive than conventional open surgical techniques that involve making a large enough opening to permit direct visual inspection of the internal surgical procedure. In particular, the term "minimally-invasive" is not restricted to the least-invasive technique possible.

Figure 1:
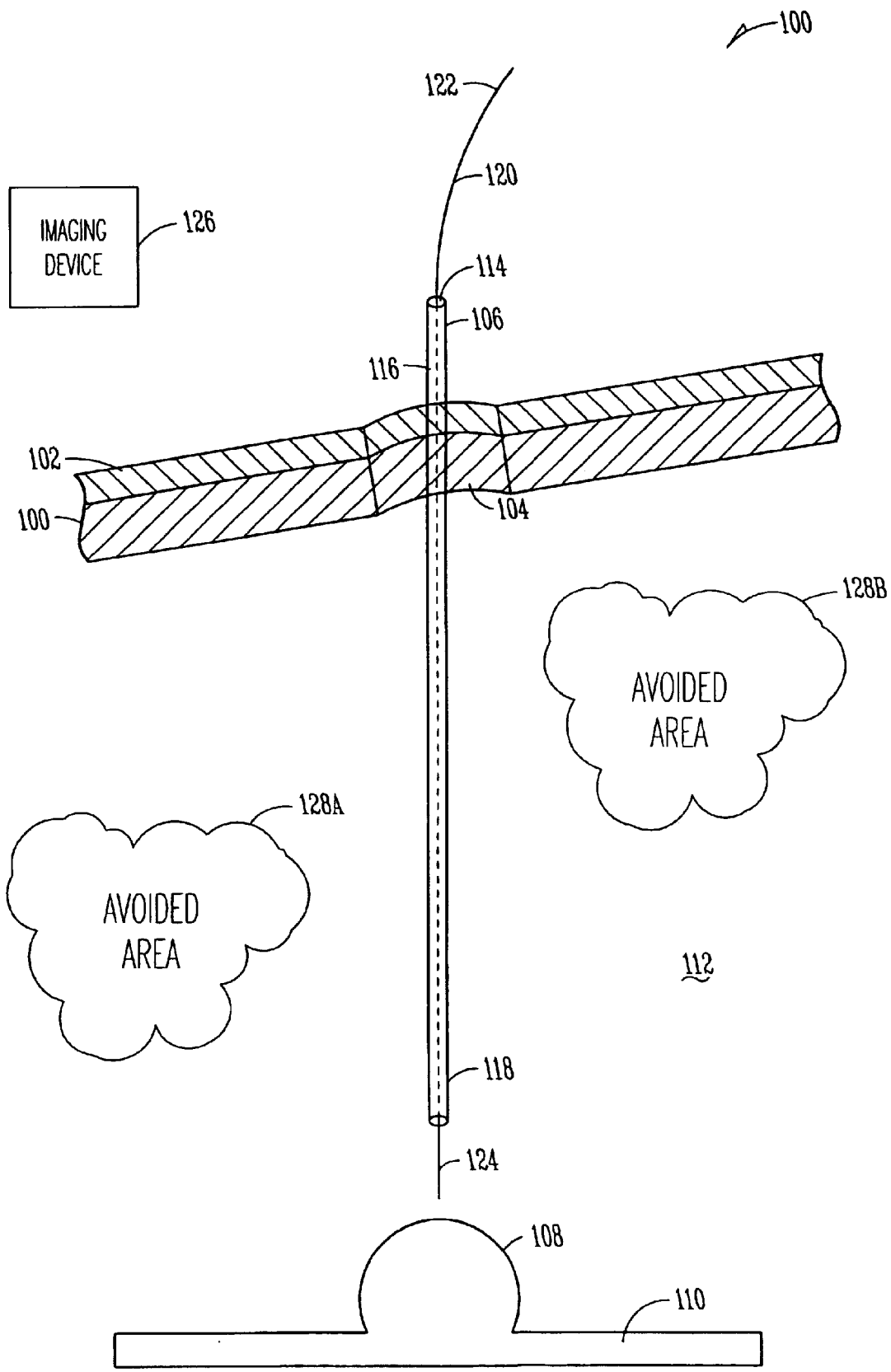
FIG. 1 is a schematic/block diagram illustrating generally an example of portions of a minimally-invasive aneurysm treatment system and portions of an environment in which it is used.

FIG. 1 is a schematic/block diagram illustrating generally an example of portions of a minimally-invasive aneurysm treatment system 100 and portions of an environment in which it is used. In this example, a portion of a top or side of a patient's skull 100 and scalp 102 are illustrated. A minimally-invasive entry opening 104 is created through skull 100 and scalp 102. In one example, opening 104 is a substantially circular burr-hole having a diameter that is approximately between 8 millimeters and 18 millimeters, such as about 14 millimeters. A exovascular probe/tube/catheter 106 (or other rigid, semi-rigid, or flexible device) is inserted through opening 104, and is directed toward an aneurysm (e.g., a saccular, globular, giant, or other aneurysm) 108 associated with blood vessel 110 within brain 112. Catheter 106 includes a lumen 114 extending between its proximal end 116 and its distal end 118. In one example, catheter 106 has an outer diameter that is less than the burr-hole diameter. In another example, catheter 106 has an outer diameter that is less than about 10 millimeters, such as an outer diameter of about 5 millimeters. In general, using a smaller outer diameter value results in less trauma to the intervening tissue. In one example, catheter 106 has an inner (i.e., lumen) diameter that is approximately between 1 millimeter and 8 millimeters, such as about 3 millimeters.

An aneurysm treatment device 120 is inserted through lumen 114 in catheter 106. Aneurysm treatment device 120 includes a proximal end 122 and a distal end 124. Distal end 124 of aneurysm treatment device 120 includes a device for altering a morphology of aneurysm 108, such as to reduce the risk of its rupture. Such aneurysm treatments include, by way of example, but not by way of limitation, clipping, clasping, snaring, looping, hooking, stapling, applying electrical energy to diathermically heat and/or electrocauterize, grasping, retrieving, securing, and/or aspirating the contents of an aneurysm. The devices for performing such treatments may be mechanical, chemical and/or electromagnetic. The choice of an appropriate treatment will depend on the size, location, and type of aneurysm.

Because minimally-invasive opening 104 is generally too small to permit convenient direct visualization, this example of system 100 includes an alternative remote external imaging device 126 to assist the surgeon in guiding distal tip 118 of catheter 106 to aneurysm 108 while avoiding areas 128A–B of brain 112. In one example, imaging device 126 is a magnetic resonance (MR) imaging device and/or a computed tomography (CT) imaging device providing real-time and/or preoperative images for guiding catheter to aneurysm 108 and then treating aneurysm 108. Such imaging modalities allow the surgeon to view images that include information about the three dimensional morphology of the aneurysm, the vessel associated with the aneurysm, and any nearby major and perforating vessels in and around the base of the aneurysm. The information yielded by such imaging modalities is advantageous for deciding whether and how to proceed with the aneurysm treatment, or for selecting a particular device or method for treating the aneurysm. In one example, an MR or CT imagable fiducial structure is positioned at a predetermined location at one or both of distal end 118 of catheter 106 and/or a distal end 124 of aneurysm treatment device 120 to create a locatable image for guiding and operating that particular device. The fiducial structure may produce either a positive image on the imaging modality or, alternatively, may be recognizable by producing a contrast with the image of the surrounding brain tissue.

Figure 2:
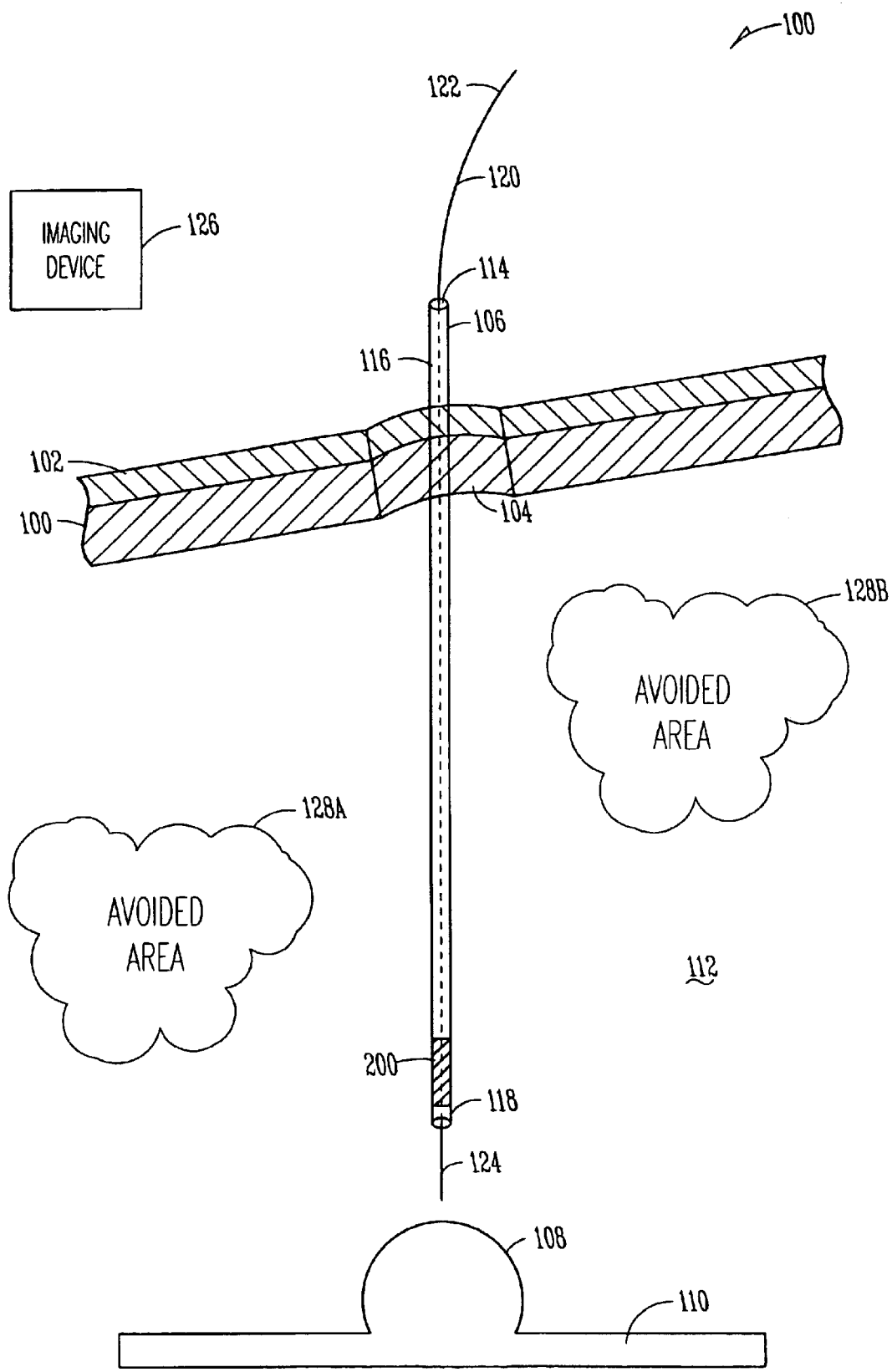
FIG. 2 is a schematic/block diagram of another example of portions of an aneurysm treatment system, in which a distal tip of a catheter also includes a local imaging device for providing enhanced visualization of nearby regions, such as an aneurysm and nearby blood vessels and brain tissue or other structures.

FIG. 2 is a schematic/block diagram of another example of portions of aneurysm treatment system 100 in which distal tip 118 of catheter 106 also includes a local imaging device 200 for providing enhanced visualization of nearby regions, such as aneurysm 108 and nearby blood vessels and brain tissue or other structures. In one example, local imaging device 200 includes at least one microcoil for local MR imaging. Some suitable microcoil examples are described in: Truwit et al. U.S. Pat. No. 5,964,705 entitled "MR-COMPATIBLE MEDICAL DEVICES;" Kucharczyk et al. U.S. patent application Ser. No. 09/448,720, filed on Nov. 24, 1999, entitled "MR-COMPATIBLE DEVICES;" Viswanathan et al. U.S. patent application Ser. No. 09/532,145, filed on Mar. 21, 2000, entitled "A DEVICE FOR HIGH GAIN AND UNIFORMLY LOCALIZED MAGNETIC RESONANCE IMAGING;" Viswanathan U.S. patent application Ser. No. 09/532,667, filed on Mar. 21, 2000, entitled "A MICROCOIL DEVICE FOR LOCAL, WIDE FIELD-OF-VIEW AND LARGE GAIN MAGNETIC RESONANCE IMAGING;" and Viswanathan U.S. patent application Ser. No. 09/532,037, filed on Mar. 21, 2000, entitled "A MICROCOIL DEVICE WITH A FORWARD FIELD-OF-VIEW FOR LARGE GAIN MAGNETIC RESONANCE IMAGING." Each of these documents is incorporated herein by reference in its entirety, and also for their collective disclosure of microcoil examples and related techniques and their equivalents. In one example, one or more of such microcoils is molded into distal end 118 of catheter 106, with appropriate connection wires extending along the length of elongate catheter 106 to its proximal end 116 for coupling to imaging device 126 or other suitable device for delivering and/or receiving energy for performing the local imaging.

Such microcoils typically enhance the visual resolution of the imaging at the working distal end 118 of catheter 106 or other probe. This actively-visible deployment probe improves the surgeon's ability to visualize the overall structure and position of the aneurysm as well as any branching capillaries or perforators that might be extending from the aneurysm or its vicinity. This can be important in ensuring effective treatment of the aneurysm. Moreover, such localized imaging allows the surgeon to avoid damaging such ancillary vessels, thereby preserving needed blood flow through such vessels to surrounding tissue. Alternatively, it allows the surgeon to also provide similar or different treatment to such ancillary vessels, where appropriate. In one example, imaging of ancillary vessels permits the surgeon to cauterize one or more of such vessels to avoid possible hemorrhaging and/or related complications.

Figure 3:
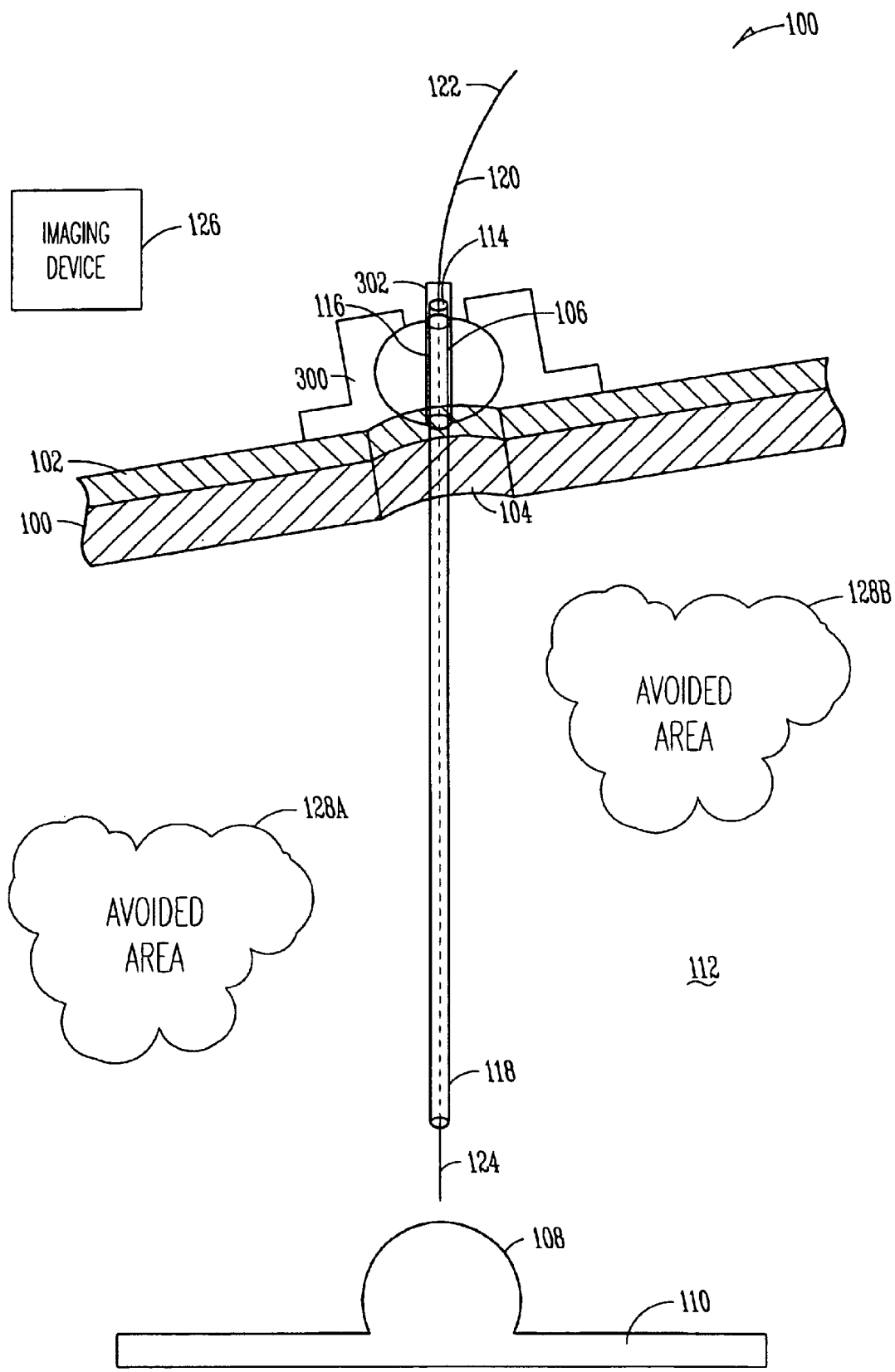
FIG. 3 is a schematic/block diagram of a further example of portions of an aneurysm treatment system, further including an entry device located at, in, and/or around an entry opening.

FIG. 3 is a schematic/block diagram of a further example of portions of system 100 further including an entry device 300 located at, in, and/or around minimally-invasive entry opening 104. In this example, ball-and-socket-type entry device 300 includes a stem-like cylindrical trajectory guide 302 that is used in conjunction with imaging device 126 to determine and lock-in a desired trajectory from opening 104 to aneurysm 108. Suitable examples of skull-mounted entry device 300, and ancillary devices and techniques for introducing a medical instrument such as catheter 106, are described in: Truwit et al. U.S. Pat. No. 6,195,577 B1 entitled "METHOD AND APPARATUS FOR POSITIONING A DEVICE IN A BODY;" Truwit U.S. patent application Ser. No. 09/058,092, filed on Apr. 9, 1998, entitled "TRAJECTORY GUIDE AND METHOD OF USE IN MAGNETIC RESONANCE AND COMPUTERIZED TOMOGRAPHIC SCANNERS;" Skakoon et al. U.S. patent application Ser. No. 09/828,451, filed on Apr. 6, 2001, entitled "DEEP ORGAN ACCESS DEVICE AND METHOD;" Mazzocchi U.S. Provisional Patent Application No. 60/225,952, filed on Aug. 17, 2000 entitled "IMPROVED TRAJECTORY GUIDES FOR SURGICAL INSTRUMENTS;" Skakoon et al. U.S. patent application Ser. No. 09/827,266, filed on Apr. 5, 2001, entitled "MEDICAL DEVICE INTRODUCER." Each of these documents is incorporated by reference in its entirety, and particularly for their description of entry devices, trajectory guides, and ancillary devices and techniques and their equivalents.

Figure 4:
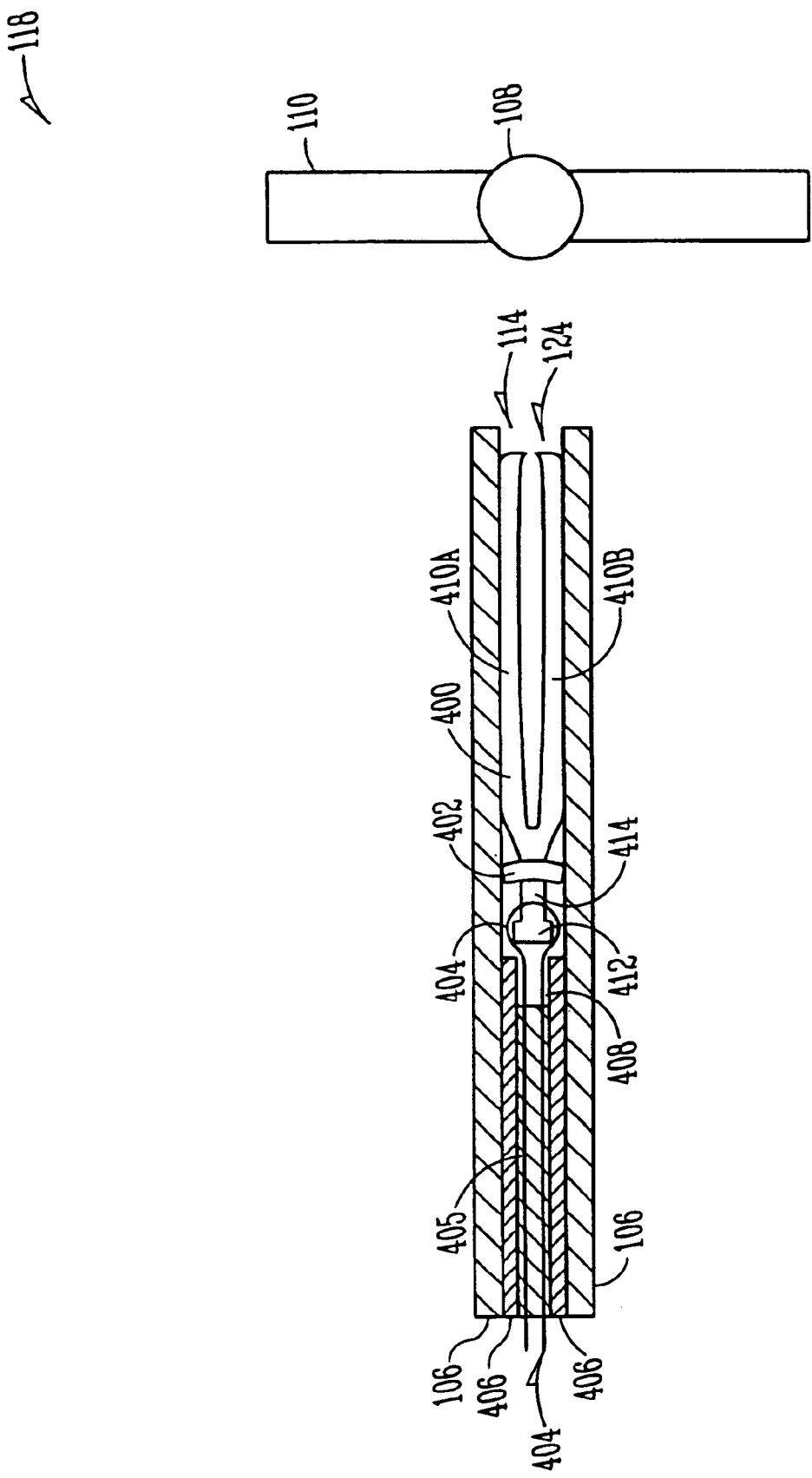
FIG. 4 is a cross-sectional schematic diagram illustrating generally an example of a distal end of a catheter. Disposed in a retracted position within a lumen of the catheter is distal end of an example aneurysm treatment device.
Figure 5:
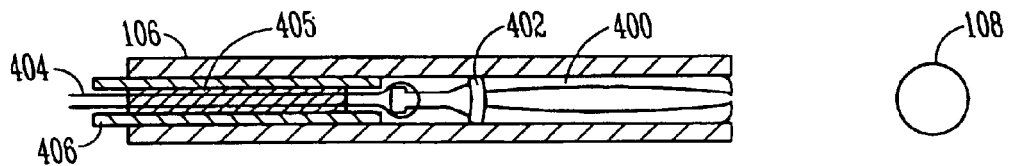
FIG. 5 includes several cross-sectional diagrams illustrating generally one technique for operating the aneurysm treatment device of FIG. 4.
Figure 5:
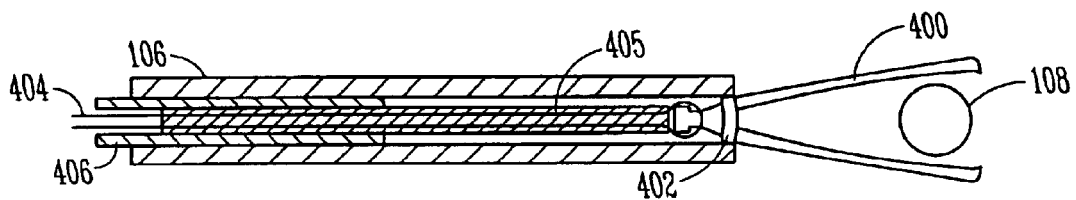
Figure 5:
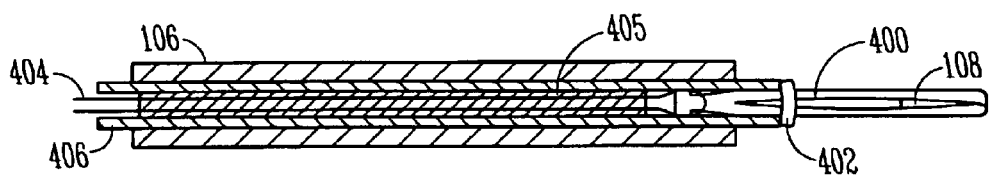
Figure 5:
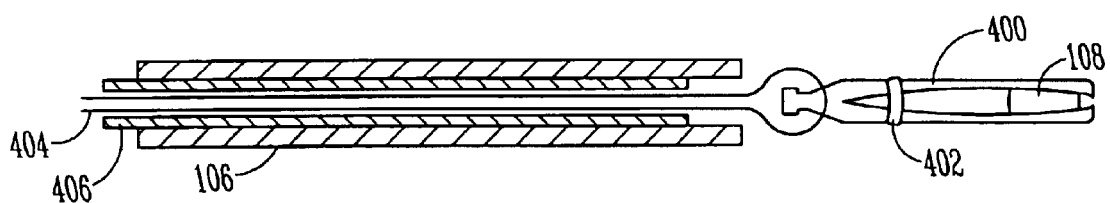

FIG. 4 is a cross-sectional schematic diagram illustrating generally an example of distal end 118 of catheter 106. Disposed in a retracted position within lumen 114 of catheter 106 is distal end 124 of an example aneurysm treatment device 120. In this example, aneurysm treatment device 120 includes a clip 400, an O-shaped ring 402 (or C-shaped partial ring), a wire-like retaining strand 404 snaring clip 400 (or other retention device), a middle tube 406 having a lumen 408 therethrough, and an inner tube 405 also having a lumen therethrough through which a portion of strand 404 extends. In this example, clip 400 is a molded plastic clip having a normally-open shape-memory property. When it is pushed out of lumen 114, such as by inner tube 405, jaws 410A–B of clip 400 spring open apart from each other such that clip 400 is in a substantially open position. Jaws 410A–B are then positioned around a desired portion of aneurysm 108 (such as around a neck portion at which aneurysm 108 extends from vessel 110, but leaving enough tissue to bridge the gap in the wall of the vessel created by the aneurysm). Then, jaws 410A–B are closed around the desired portion of aneurysm 108. In one example, this is accomplished by firmly holding retaining strand 404, which is looped around a knob 412 or within a groove 414 of clip 400, while pushing middle tube 406 out from lumen 114. In this manner, middle tube 406 engages ring 402 and pushes ring 402 out around jaws 410A–B. This closes jaws 410A–B around the desired portion of aneurysm 108, so that clip 400 is in its substantially closed position. Then, by manipulating the proximal end of retaining strand 404, its looped distal end is pushed out slightly to open sufficiently to disengage retaining strand 404 from clip 400, so that clip 400 is freed and left behind to clip the desired portion of aneurysm 108 to reduce its risk of rupture. In one example, inner tube 405 is optionally withdrawn to promote loosening and disengaging retaining strand 404 from clip 400. Retaining strand 404, middle tube 406, inner tube 405, and catheter 106 are then withdrawn from brain 112, and minimally-invasive opening 104 is closed. FIG. 5 includes several cross-sectional diagrams illustrating generally one technique for operating this example of aneurysm treatment device 120 of FIG. 4.

The example illustrated in FIGS. 4 and 5 includes many variations within its scope. In one such variation, retaining strand 404 includes a third strand extending through lumen 114 and coupled to a collar around the illustrated looped pair of strands of retaining strand 404. By tightening or loosening the collar by manipulating the third strand, the loop is more securely opened or closed to respectively release or retain clip 400. In another example, retaining strand 404 (which need not be a loop, but is alternatively a single strand affixed to a portion of clip 400), includes a pre-weakened breakaway portion at or near clip 400. By pulling back on the proximal end of retaining strand 404 while pushing out on middle tube 406 to close jaws 410A–B of clip 400 using ring 402, the pre-weakened portion of retaining strand 404 breaks at a predefined degree of tension. This releases closed clip 400. The proximal portion of retaining strand 404 is then removed. Middle tube 406 and catheter 106 are also withdrawn from brain 112. In another variation, distal end 118 of catheter 106 includes an inward extending longitudinal slot that is shaped to permit one of jaws 410A–B to spring outward toward its substantially open position even before clip 400 is extended out of lumen 114. This permits clip 400 to open around aneurysm 108 along the side of catheter 106 rather than concentrically outward.

Figure 6:
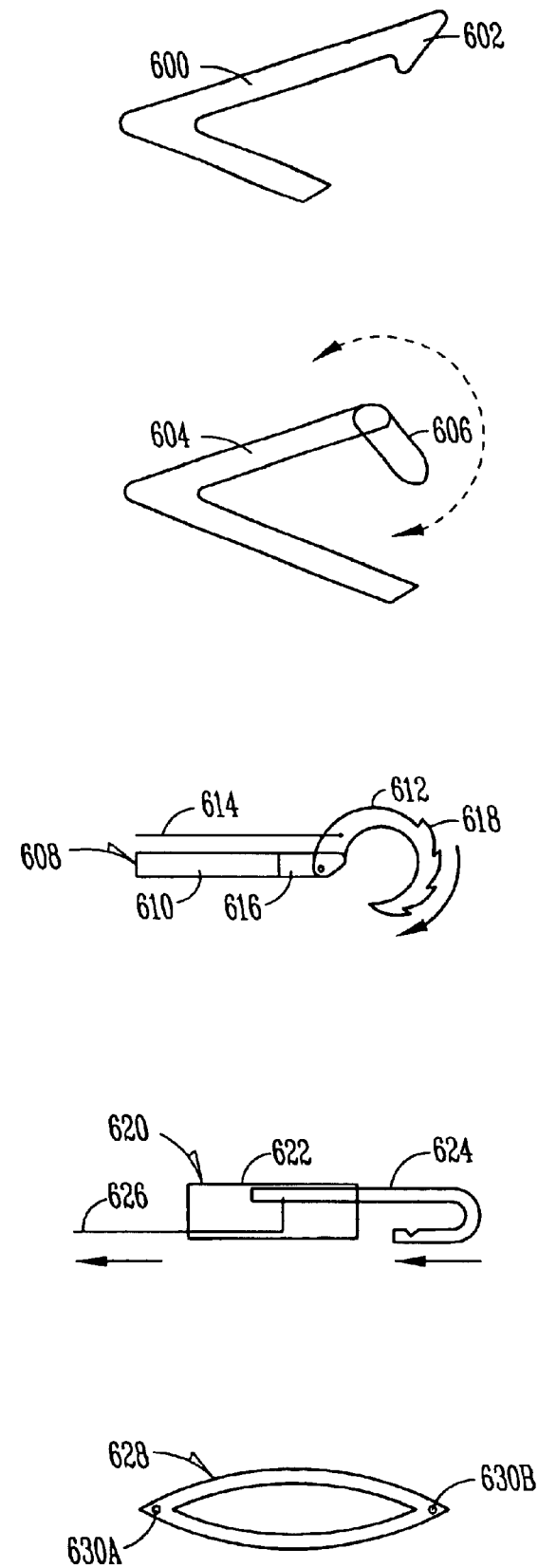
FIG. 6 is a schematic illustration of several alternative components for aneurysm-clipping in an aneurysm treatment device.

FIG. 6 is a schematic illustration of several alternative components for aneurysm-clipping in an aneurysm treatment device. In the examples of FIG. 6, clip 600 includes distal hook 602 or other self-locking mechanism that avoids the need for a separate sliding ring 402 to close and/or retain clip 600 in its substantially closed position. In this example, clip 600 has a normally-open shape-memory property. Clip 600 may be delivered through catheter 106 and closed by a middle tube 406 or any other suitable technique.

Clip 604 includes another example of a self-locking mechanism, such as a ring 606 located at a distal end of one of its jaws. This self-locking mechanism moves (e.g., rotates) to engage the distal end of the opposing jaw to retain normally-open clip 604 in its substantially-closed position. Clip 604 may also be delivered through catheter 106 and closed by a middle tube 406 or other suitable technique.

Clip 608 is an example of a geared latch hook device that is delivered through catheter 106 and closed around a portion of aneurysm 108. In this example, clip 608 includes a body portion 610 and a hook portion 612. It also includes a resilient strand 614 or shaft that extends to proximal end 116 of catheter 106. By pushing on a proximal end of strand 614, curved hook portion 612 is closed around aneurysm 108. A distal portion of curved hook portion is received by hole 616 in clip body 610. One or more teeth 618 on hook 612 engages a pawl-like device associated with hole 616, allowing hook 612 to clasp and retain aneurysm 108. Body 610 and strand 614 are releasably coupled to hook 612 by any suitable releasable fastening technique. Some suitable examples include, by way of example, but not by way of limitation, a pre-weakened breakaway portion, a rotatably-releasable strand or shaft, and/or a threaded coupler.

Clip 620 is an example of another aneurysm clip or clasp that is delivered through catheter 106 and closed around aneurysm 108. In this example, clip 620 includes a body 622 portion and a hooked shaft 624 portion that operate together in a padlock-like fashion to clasp and retain aneurysm 108. Strand or shaft 626 engages hooked shaft 624 to pull it back, thereby clasping the desired portion of aneurysm 108 between hooked shaft 624 and body 622 of clip 620. Strand 626 releasably engages hooked shaft 624, such as by one of the above-described releasable fastening techniques, or by simply receiving a hooked or other suitably shaped portion of a distal end of strand 626 in a slot or other suitable opening from which it can be disengaged by manipulating the proximal end of strand 626.

Clip 628 is an example of yet another aneurysm clip or clasp that is delivered through catheter 106 and closed around aneurysm 108. In this example, clip 628 is a double bow-like clasp having a normally-closed shape-memory property. After being delivered through catheter 106, tension is applied to force its midregions outward so that aneurysm 108 can be positioned therebetween. One technique for applying such tension is to use one or more resilient strands or shafts that releasably engage features on clip 628 (e.g., receptacles 630A–B). In an alternative example, clip 628 includes a normally-open shape-memory property. Such a normally-open clip 628 is closed around aneurysm 108 using a suitable closure technique, such as by using a middle tube 406 to push a surrounding ring 402 out around normally open clip 628 to close it around aneurysm 108.

Figure 7:
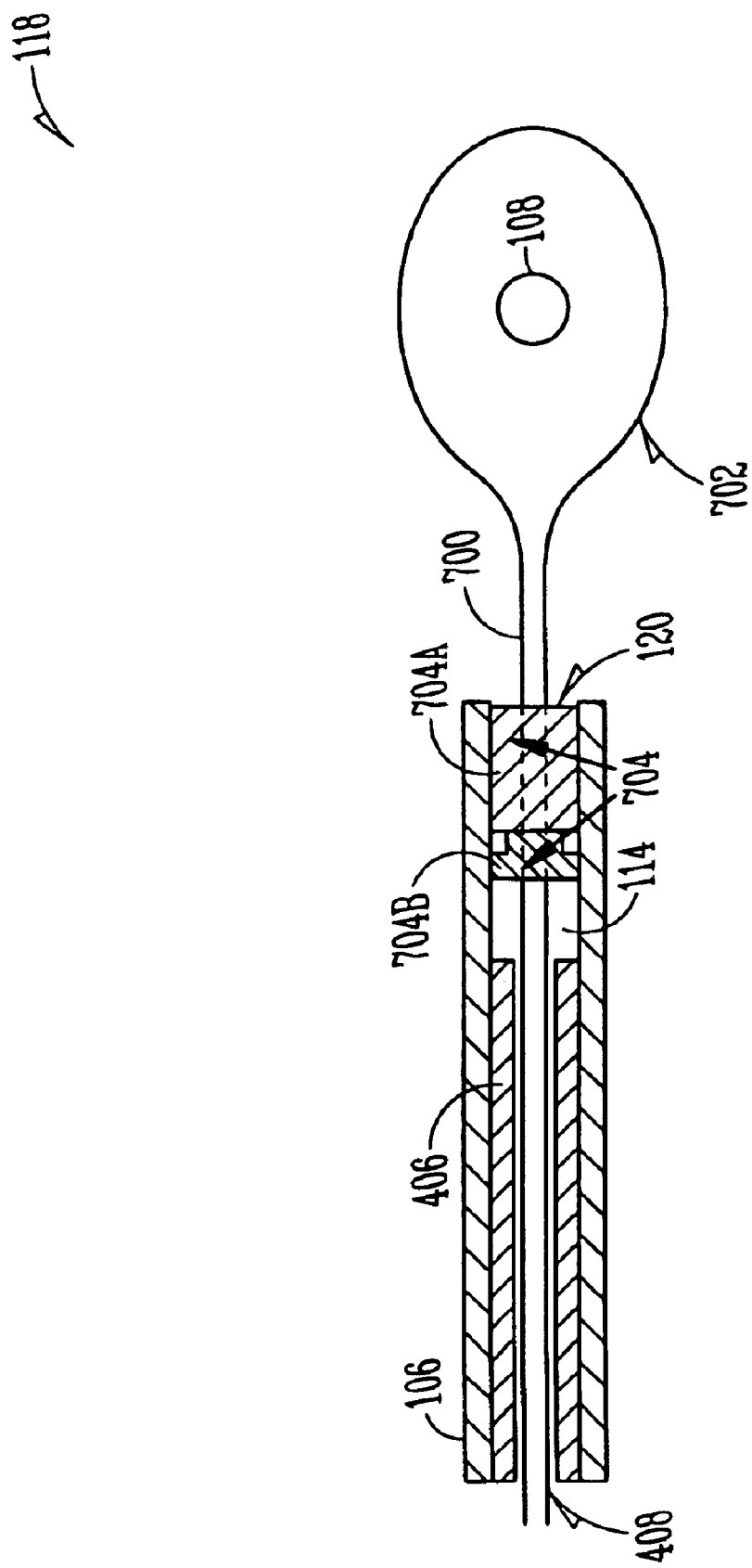
FIG. 7 is a cross-sectional schematic diagram illustrating generally another example of a distal end of a catheter, the distal end including a lumen through which another example aneurysm treatment device is disposed for treating an aneurysm.

FIG. 7 is a cross-sectional schematic diagram illustrating generally another example of distal end 118 of catheter 106, the distal end 118 including a lumen 114 through which another example aneurysm treatment device 120 is disposed for treating aneurysm 108. In this example, aneurysm treatment device 120 includes a wire-like snare 700 having at least one strand that extends through lumen 114 of catheter 106 from its proximal end 116 to its distal end 118, and extending outward from distal end 118 in a loop 702. In its substantially open position, as illustrated in FIG. 7, loop 702 is large enough to encircle a desired portion of aneurysm 108. In this example, snare 700 extends through a unidirectional retention mechanism, such as cuff 704, in lumen 114 at distal end 118 of catheter 106. In this example, cuff 704 includes two pieces 704A–B that lock when snare 700 is rotated after loop 702 is pulled snugly around aneurysm 108 to tie off aneurysm 108. In one example, snare 700 includes a pre-weakened breakaway portion that is slightly more proximal than cuff 704, so that when the user pulls firmly back on the proximal end of snare 700 with sufficient tension, snare 700 breaks away to leave behind loop 702, around aneurysm 108, and securing cuff 704. In this example, aneurysm treatment device 120 also includes a middle tube 406 having a lumen 408 through which a portion of snare 700 extends. The user pushes on the proximal end of middle tube 406 to push against cuff 704, while the proximal end of snare 700 is being pulled back, to break the pre-weakened portion of snare 700. Then, the user further pushes on the proximal end of middle tube 406 to push out and release cuff 704 and the tightened loop portion of snare 700. In an alternative example, in which snare 700 need not include a pre-weakened portion, cuff 704 includes a blade-like projection that cuts a portion of snare 700 to release loop 702 after it is secured around aneurysm 108. In addition to cuff 704, other modes of unidirectional retention devices operating noose-like loops 702 include a toothed or other structure operating similarly to a plastic cable-tie and/or a bag-tie, or a pawl or other ratcheting/escapement mechanism that allows loop 702 to be securely tightened around aneurysm 108.

Figure 8:
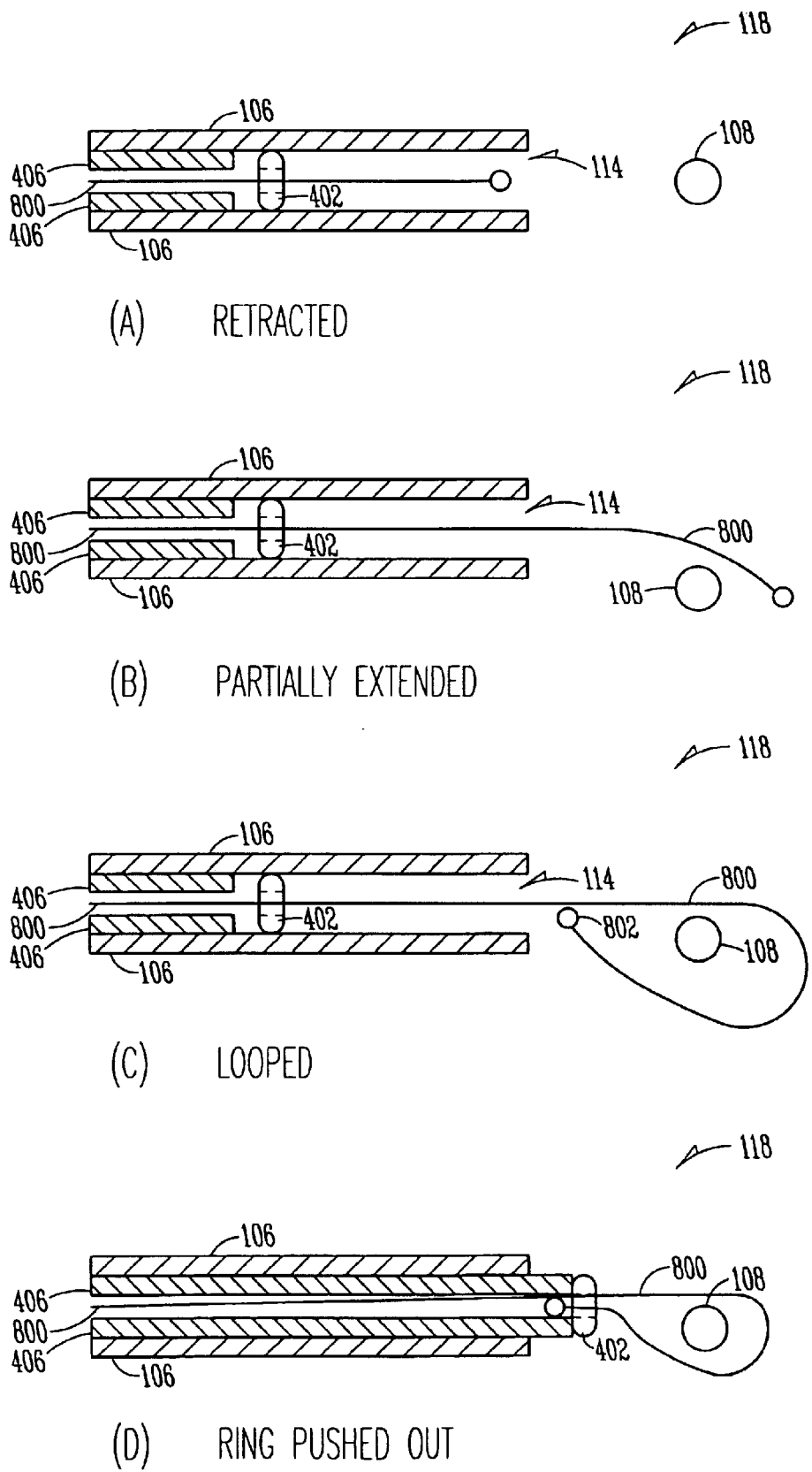
FIG. 8 includes several cross-sectional diagrams illustrating another example of a distal portion of a snare-like aneurysm treatment device that includes a strand, the end of which has a normally-looped shape-memory property.

FIG. 8 includes several cross-sectional diagrams illustrating another example of a distal portion of a snare-like aneurysm treatment device 120 that includes a strand 800, the end of which has a normally-looped shape-memory property. In this example, strand 800 extends from proximal end 116 to distal end 118 of catheter 106 through its lumen 114, through a central lumen of a middle tube 406, and through a central lumen of ring 402. A distal end of strand 800 is extended out from the distal end 118 of catheter 106 for a sufficient distance to allow its shape-memory property to hook the distal end of strand 800 around the desired portion of aneurysm 108. In this example, the distal end of strand 800 includes a catch 802 (e.g., a ball, a grooved ball, a hook, or any other suitable structure). Catch 802 engages a more proximal portion of strand 800 after being hooked around the desired portion of aneurysm 108. Middle tube 406 is then used to push ring 402 out over catch 402. Then, the proximal end of strand 800 is pulled back to draw a noose-like loop to clamp off the desired portion of aneurysm 108. In one example, strand 800 includes a more proximal pre-weakened portion that breaks away when sufficient tension is applied, leaving behind the loop and ring tying off aneurysm 108. In an alternative example, a portion of strand 800 includes a toothed or other structure operating similarly to a plastic cable-tie and/or a bag-tie, or a pawl or other ratcheting/escapement mechanism, as discussed above, to retain the now-looped hook snare in its substantially closed position around aneurysm 108. In another alternative example, ring 402 is omitted, and catch 802 includes a hook or other suitable structure that catches a more proximal portion of strand 800 when its proximal end is drawn back to break away a pre-weakened portion of strand 800 that is more proximal than the engaged hook.

Figure 9:
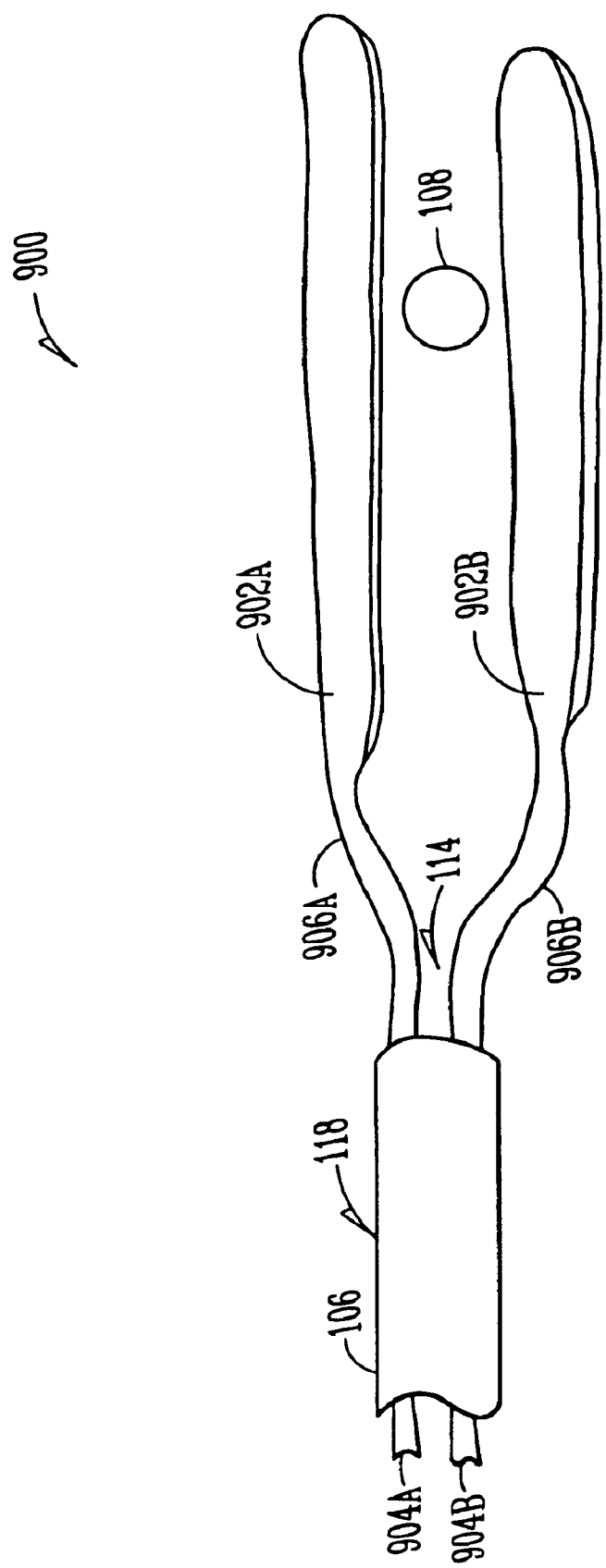
FIG. 9 is a perspective view illustrating another example of an aneurysm treatment device, which includes a pair of electrodes that are exovascularly delivered through a lumen of a catheter.

FIG. 9 is a perspective view illustrating another example of an aneurysm treatment device 900. In this example, aneurysm treatment device 900 includes a pair of electrodes 902A–B that are exovascularly delivered through lumen 114 of catheter 106. In the illustration of FIG. 9, electrodes 902A–B are elongate paddles extending outward from respective insulated stylet shafts 904A–B at resiliently flexible outward necked portions 906A–B. In this manner, when electrodes 902A–B are extended out of lumen 114 at distal end 118 of catheter 106, they spring outward into a substantially open position to allow aneurysm 108 to be positioned therebetween. By then either sliding catheter 106 out over necked portions 906A–B, or by then pulling back necked portions 906A–B into lumen 114 at distal end 118 of catheter 106, electrodes 902A–B are forced together into a substantially closed position, clamping aneurysm 108 therebetween. Electrical energy is then applied between proximal ends of the insulated stylet shafts 904A–B and conducted to electrodes 902A–B to cauterize shut the clamped portion of aneurysm 108. Electrodes 906A–B are then again manipulated into their substantially open position and retracted together with catheter 106.

Figure 10:
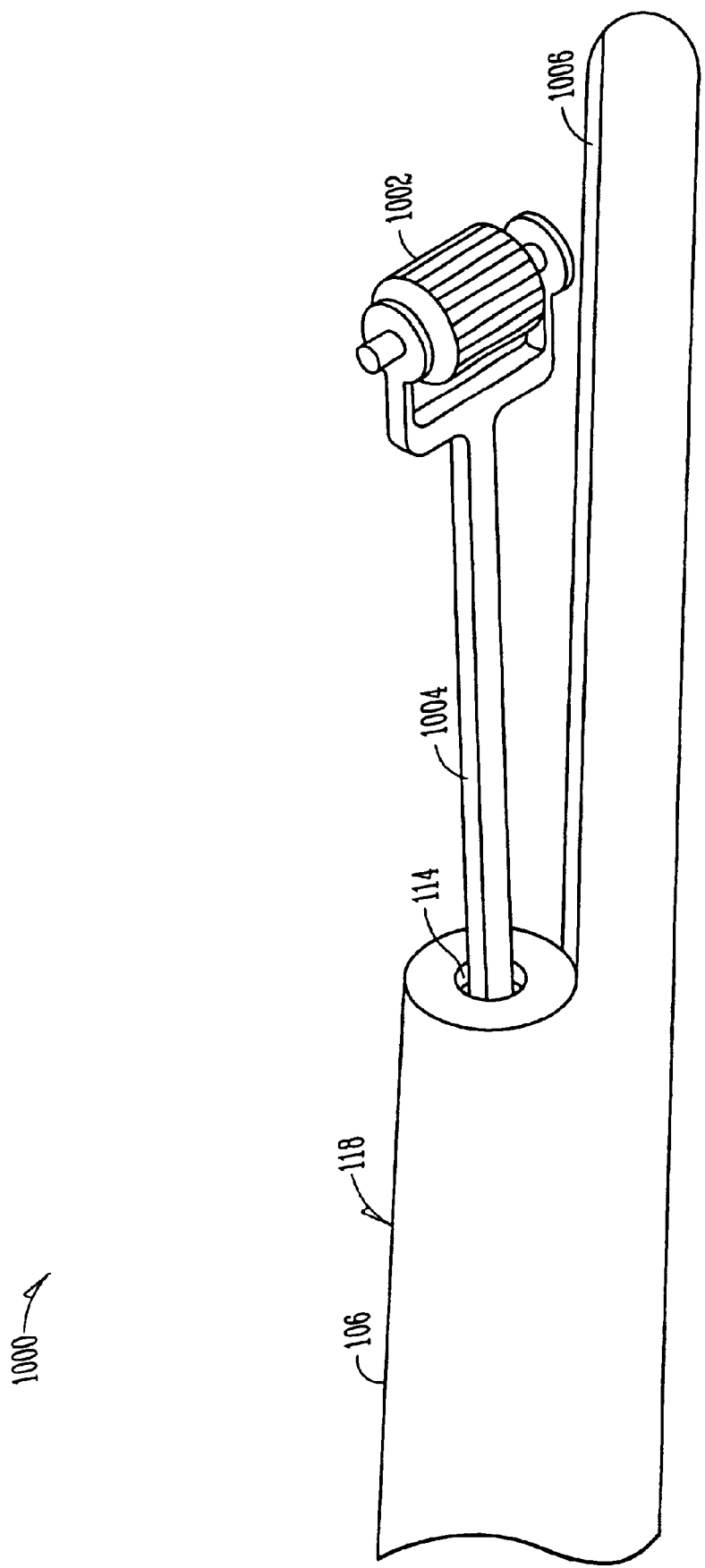
FIG. 10 is a perspective view illustrating another example of an aneurysm treatment device including a movable electrode and a fixed electrode.

FIG. 10 is a perspective view illustrating another example of an aneurysm treatment device 1000 including a movable electrode and a fixed electrode. In this example, aneurysm treatment device 1000 includes a movable electrode 1002 extending out from lumen 114 at distal end 118 of catheter 106 on an electrically insulated stylet shaft 1004. A flat fixed electrode 1006 is formed integrally with distal end 118 of catheter 106, extending outwardly therefrom, with an associated conductor coupling it to proximal end 116 of catheter 106. In this example, fixed electrode 1006 is first positioned adjacent to aneurysm 108. Then, movable electrode 1002 is extended out around the other side of aneurysm 108. In this example, movable electrode 1002 includes a rolling electrode that is rolled back and/or forth along aneurysm 108, by manipulating a proximal end of shaft 1004, to clamp the desired portion of aneurysm 108 between the electrodes 1002 and 1006 as electrical energy is applied to cauterize shut the desired portion aneurysm 108.

Figure 11:
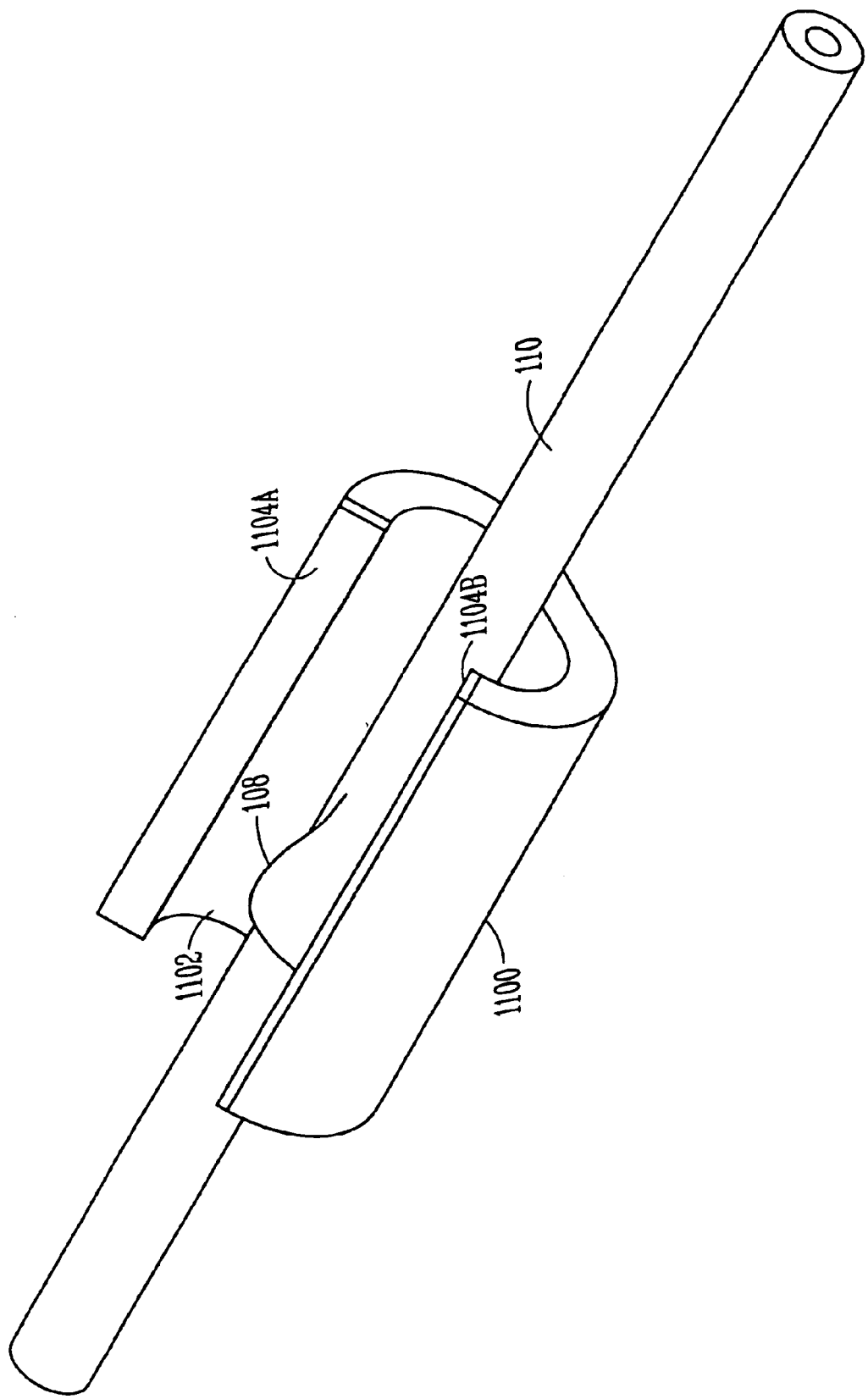
FIG. 11 is a perspective view illustrating another example of a catheter-delivered aneurysm treatment device, which in this case includes a C-channel clamp shaped for being fitted around an exterior portion of a blood vessel and clamping a desired portion of an aneurysm therebetween.

FIG. 11 is a perspective view illustrating another example of a catheter-delivered aneurysm treatment device, which in this case includes a C-channel clamp 1100 shaped for being fitted around a portion of blood vessel 110 and clamping a desired portion of aneurysm 108 therebetween. In one technique, C-channel clamp 1100 is mounted on the tip of a stylet shaft having a sufficient diameter to keep channel 1102 sufficiently open to slide around the desired portion of aneurysm 108 when the stylet shaft is extended out of distal tip 118 of catheter 106. A second stylet (or a middle tube, such as middle tube 406) is used to slide C-channel clamp 1100 off the first stylet into place around vessel 110 and aneurysm 108. In this example, C-channel clamp 1100 has a normally-closed shape-memory property, so that it closes around the desired portion of aneurysm 108 after it is slid into place off of the first stylet shaft. In a further example, electrically insulative C-channel clamp 1100 also includes conductive electrodes 1104A–B located along the edges of its C-channel for cauterizing closed the clamped portion of aneurysm 108. In this example, electrodes 1104A–B include receptacles, at any suitable location, for subsequent access by conductors delivering the electrical cautery energy after the delivery stylet(s) are removed from lumen 114 of catheter 106.

Figure 12:
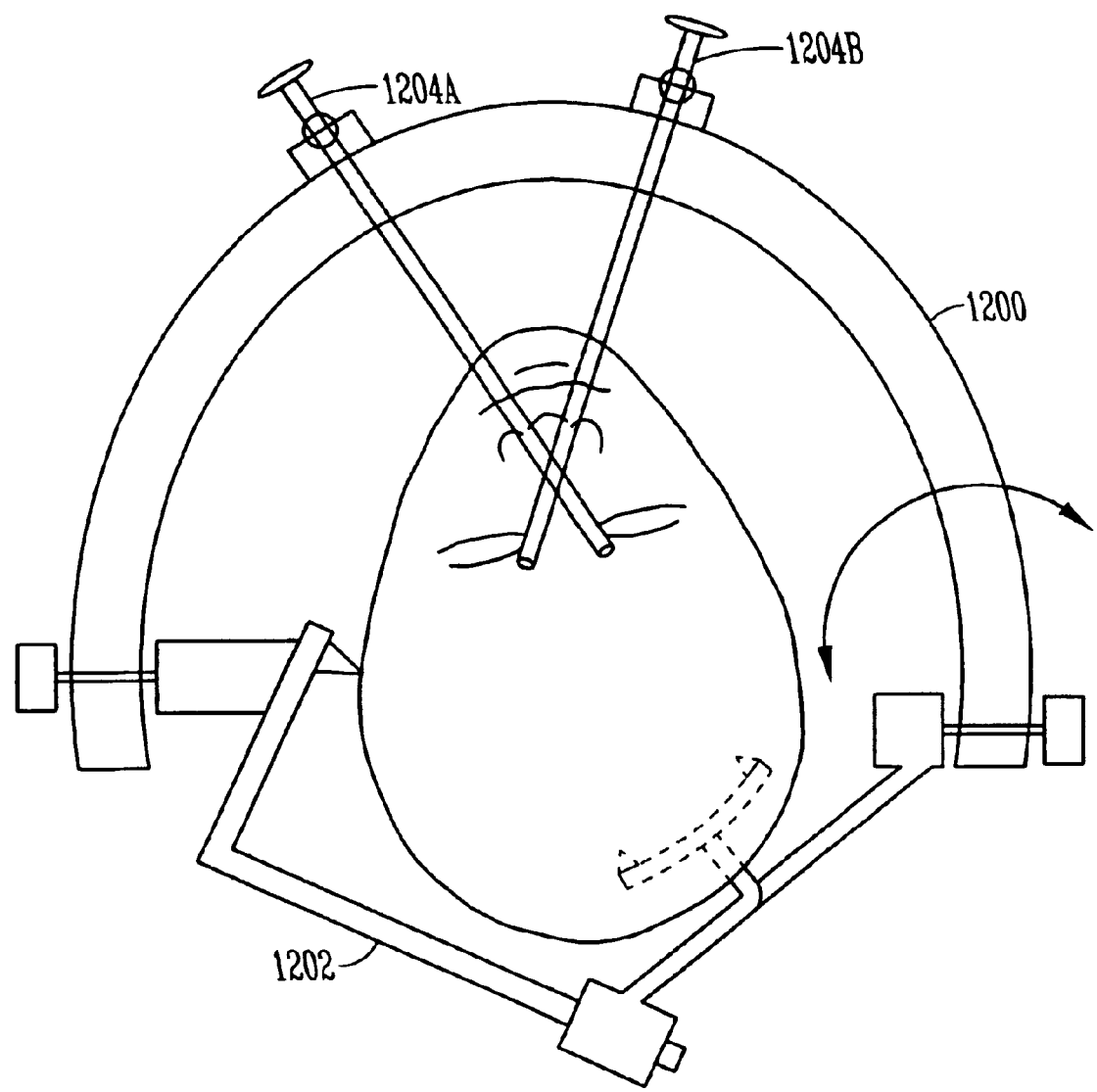
FIG. 12 is a perspective view illustrating a number of possible variations of the minimally-invasive aneurysm treatment techniques discussed above, such as nasalpharyngeal access, frame-mounted entry devices, using a plurality of minimally-invasive devices, and/or using separate minimally-invasive devices for imaging and aneurysm treatment.

FIG. 12 is a perspective view illustrating a number of possible variations of the minimally-invasive aneurysm treatment techniques discussed above, such as nasalpharyngeal access, frame-mounted entry devices, using a plurality of minimally-invasive devices, and/or using separate minimally-invasive devices for imaging and aneurysm treatment. For example, while FIG. 3 illustrated access through the top or the side of a patient's skull, FIG. 12 illustrates a nasalpharyngeal node of access through a patient's nose and sinuses. In this example, a rotatable arc-like frame 1200 is mounted to a head holding device 1202. One or more entry devices, such as ball-and-socket trajectory-guide bearing entry devices 1204A–B, is mounted to a suitable location on frame 1200. In one example, such as illustrated in FIG. 12, a first entry device (e.g., entry device 1204A) is used to provide an image-guided trajectory of a catheter-delivered aneurysm treatment device to a target aneurysm (for example, using the above-discussed clip, electrocautery electrodes, etc.). A second entry device (e.g., entry device 1204B) is used to establish a trajectory and introduce a minimally-invasive localized imaging modality (e.g., a microcoil for localized MRI, an endoscope for optical visualization, and ultrasound probe, etc.).

In the examples of FIGS. 1–12, example materials suitable for constructing catheter 106, middle tube 406, inner tube 405, and/or cuff 704 include, by way of example, but not by way of limitation, one or a combination of nonmagnetic carbon fiber, titanium, rigid or semi-rigid extruded plastic, polyetheretherketone (PEEK), and/or polyurethane. In a non-MR (e.g., CT) environment, in which nonmagnetic components are not required, stainless steel is also an example of a suitable material for these components. Example materials suitable for constructing ring 402, clip 400, clip 600, clip 604, clip 608, clip 620, and/or clip 628 include, by way of example, but not by way of limitation, one or a combination of titanium, polyurethane, polyolefin, polyethylene, and/or polypropylene. Examples of suitable materials for constructing strand 404 and/or snare 700 include, by way of example, but not by way of limitation, one or a combination of titanium, tungsten, platinum-iridium, an extruded plastic monofilament, nylon, and/or KEVLAR.® Moreover, strand 404 could be constructed from a twisted pair of strands constructed from the same or different ones of these or other materials. Examples of suitable materials for constructing hook/snare portion of strand 800 include, by way of example, but not by way of limitation, nickel-titanium (nitonol) and/or other suitable nonmagnetic memory metal. Examples of suitable materials for constructing electrodes 902A–B, electrode 1002, electrode 1006, and/or electrodes 1104A–B include, by way of example, but not by way of limitation, one or a combination of platinum-iridium and/or other nonmagnetic conductive material. Examples of suitable materials for constructing frame 1200 include, by way of example, but not by way of limitation, one or more of aluminum and/or other rigid nonmagnetic material.

It is to be understood that the above description is intended to be illustrative, and not restrictive. For example, the above-discussed embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein."

What is claimed is:

1. A system including:
   an elongate exovascular probe, including proximal and distal ends, the probe including an outer dimension that is less than about 18 millimeters to permit the probe to be introduced through a similarly-sized minimally-invasive opening in a portion of a subject's skull and exovascularly advanced along a longitudinal axis of the probe to an aneurysm within the skull; and
   an aneurysm treatment device carried by the probe and dimensioned to permit the aneurysm treatment device to be introduced through the opening, at least a distal portion of the aneurysm treatment device being releasable via axial translation of at least a portion of the probe without lateral motion of the probe with respect to the probe axis, to grasp about the aneurysm.

2. The system of claim 1, further including an imaging device to permit viewing of an image of both the aneurysm treatment device and the aneurysm.

3. The system of claim 2, in which the imaging device includes a magnetic resonance (MR) imaging device.

4. The system of claim 3, in which the imaging device further includes a local MR imaging device near the distal end of the probe.

5. The system of claim 4, in which the local MR imaging device includes at least one microcoil.

6. The system of claim 1, in which at least one of the aneurysm treatment device and the distal end of the probe includes at least one of an MR or CT imagable fiducial structure.

7. The system of claim 1, in which the probe and aneurysm treatment device are both at least one of MR or CT compatible.

8. The system of claim 1, in which the aneurysm treatment device includes a structure having substantially open and substantially closed positions, wherein the open position is sized to permit at least one portion of the aneurysm treatment device to be positioned around at least a portion of at least one of a saccular, globular, or giant aneurysm, and wherein the closed position is sized to permit the at least one portion of the aneurysm treatment device to press against at least a portion of the aneurysm.

9. The system of claim 8, in which the aneurysm treatment device structure includes a shape-memory property.

10. The system of claim 9, in which the shape-memory property, in the absence of applied bias, is associated with one of the open or closed positions.

11. The system of claim 1, further including an elongate member shaped to extend through a lumen in the probe, the elongate member releasably coupling to the aneurysm treatment device.

12. The system of claim 1, in which the aneurysm treatment device is shaped to be extendable from and retractable into a lumen of the probe.

13. The system of claim 1, in which the aneurysm treatment device includes at least one of a clip, a clasp, a snare, a loop, a hook, a staple, or an electrode.

14. The system of claim 1, in which the aneurysm treatment device includes a normally substantially open clip that is substantially closed when retracted into a lumen of the probe, and further including:
   an elongate tube shaped to extend through the lumen of the probe, a distal end of the elongate tube shaped to extend out of the distal end of the probe and around a portion of the clip to substantially close a portion of the clip around a portion of the aneurysm; and
   a flexible strand shaped to extend through the elongate tube, and releasably coupled to a portion of the clip.

15. The system of claim 14, further including a ring shaped to engage the distal end of the elongate tube, the ring shaped to encircle a portion of the clip to hold the clip in the substantially closed position around the portion of the aneurysm.

16. The system of claim 1, further including an entry device, the entry device including:
   a first securing mechanism to secure the entry device in association with the subject's skull; and
   a second securing mechanism to secure an orientation of a trajectory guide portion of the entry device to define a path between the minimally-invasive opening and the aneurysm.

17. The system of claim 16, further including an imaging device to provide information upon which the orientation of the trajectory guide is determined.

18. The system of claim 1, wherein the probe includes a substantially uniform cylindrical outer surface that is sized and shaped to be accepted within and guided by a similarly sized and shaped lumen of a trajectory guide device.

19. The system of claim 18, wherein the aneurysm treatment device carried by the probe is dimensioned to permit the aneurysm treatment device to be introduced via the trajectory guide device through the opening, at least a distal portion of the aneurysm treatment device being releasable to grasp about the aneurysm, while a proximal portion of the aneurysm treatment device is disposed within the probe and the probe is accepted within the lumen of the trajectory guide device.

20. The system of claim 1, in which the aneurysm treatment device includes at least one clip.

21. The system of claim 1, in which the aneurysm treatment device includes at least one clasp.

22. The system of claim 1, in which the aneurysm treatment device includes at least one snare.

23. The system of claim 1, in which the aneurysm treatment device includes at least one loop.

24. The system of claim 1, in which the aneurysm treatment device includes at least one hook.

25. The system of claim 1, in which the aneurysm treatment device includes at least one staple.

26. The system of claim 1, in which the aneurysm treatment device includes at least one electrode.

27. A system including:
   an elongate exovascular probe, including proximal and distal ends, the probe including an outer dimension that is less than about 18 millimeters to permit the probe to be introduced through a similarly-sized minimally-invasive opening in a portion of a subject's skull and exovascularly advanced along a longitudinal axis of the probe to an aneurysm within the skull;

an aneurysm treatment device carried by the probe and dimensioned to permit the aneurysm treatment device to be introduced through the opening, at least a distal portion of the aneurysm treatment device being releasable via axial translation of at least a portion of the probe without lateral motion of the probe with respect to the probe axis, to grasp about the aneurysm; and a local imaging device located near the distal end of the probe.

28. The system of claim 27, in which the local imaging device includes a magnetic resonance (MR) imaging device.

29. The system of claim 27, in which the aneurysm treatment device includes a structure having substantially open and substantially closed positions, wherein the open position is sized to permit at least one portion of the aneurysm treatment device to be positioned around at least a portion of an aneurysm, and wherein the closed position is sized to permit the at least one portion of the aneurysm treatment device to press against at least a portion of the aneurysm.

30. The system of claim 27, further including an entry device shaped to introduce the probe.

31. The system of claim 30, in which the entry device includes:

a first securing mechanism to secure the entry device in association with the subject's skull; and a second securing mechanism to secure an orientation of a trajectory guide portion of the entry device to define a path between the minimally-invasive opening and the aneurysm.

32. The system of claim 27, wherein the probe includes a substantially uniform cylindrical outer surface that is sized and shaped to be accepted within and guided by a similarly sized and shaped lumen of a trajectory guide device.

33. The system of claim 32, wherein the aneurysm treatment device carried by the probe is dimensioned to permit the aneurysm treatment device to be introduced via the trajectory guide device through the opening, at least a distal portion of the aneurysm treatment device being releasable to grasp about the aneurysm, while a proximal portion of the aneurysm treatment device is disposed within the probe and the probe is accepted within the lumen of the trajectory guide device.

34. A system including:

an elongate exovascular probe, including proximal and distal ends, the probe including an outer surface that is conformally sized and shaped to be accepted within and guided by a correspondingly sized and shaped lumen of a trajectory guide device, the probe also sized and shaped to permit the probe to be introduced through an opening in a portion of a subject's skull and exovascularly advanced along a longitudinal axis of the probe to an aneurysm within the skull; and an aneurysm treatment device carried by the probe and dimensioned to permit the aneurysm treatment device to be introduced via the trajectory guide device through the opening, at least a distal portion of the aneurysm treatment device being releasable via axial translation of at least a portion of the probe without lateral motion of the probe with respect to the probe axis, to grasp about the aneurysm, while a proximal portion of the aneurysm treatment device is disposed within the probe and the probe is accepted within the lumen of the trajectory guide device.

35. The system of claim 34, in which the outer surface of the probe includes a substantially cylindrical surface that is sized and shaped to be accepted within and guided by the lumen of the trajectory guide device.

36. The system of claim 35, in which the outer surface of the probe is a substantially uniform cylindrical surface.

37. The system of claim 36, in which the probe includes:

an elongate outer tube, providing the substantially uniform cylindrical outer surface of the probe that is sized and shaped to be accepted within and guided by a similarly sized and shaped lumen of a trajectory guide device, the outer tube including a longitudinal outer tube lumen; and an elongate inner tube, including a substantially uniform cylindrical outer surface that is sized and shaped to be accepted within and guided by the outer tube lumen, the inner tube including a longitudinal inner tube lumen.

38. The system of claim 37, in which the aneurysm treatment device includes a clip that is sized and shaped to fit within the inner tube lumen, when the clip is retracted into a closed position, and wherein the clip is sized and shaped to fit about a portion of an aneurysm, when the clip is expanded into an open position.

39. The system of claim 38, in which the probe further includes a strand that is sized and shaped to extend through the inner tube lumen, and wherein the strand is releasably coupled to a portion of the clip.

40. The system of claim 39, further including a ring, the ring sized and shaped to be carried within the outer tube lumen, and sized and shaped to engage a distal end of the inner tube, and sized and shaped to encircle a portion of the clip to close and hold the clip around the portion of the aneurysm.

41. The system of claim 34, further including an entry device, the entry device including:

a first securing mechanism to secure the entry device in association with the subject's skull; and a second securing mechanism to secure an orientation of a trajectory guide portion of the entry device to define a path between the minimally-invasive opening and the aneurysm.

42. The system of claim 41, further including means for providing information upon which the orientation of the trajectory guide is determined.

43. The system of claim 42, further including a local imaging device located near the distal end of the probe.

44. A system for use with a subject's skull including:

a trajectory guide having a trajectory that is fixable or fixed with respect to the subject's skull;

an elongate exovascular probe, including proximal and distal ends, the probe is sized and shaped to be guided along the trajectory by the trajectory guide, the probe also includes an outer dimension that is less than about 18 millimeters to permit the probe to be introduced through a similarly-sized minimally-invasive opening in a portion of the subject's skull and exovascularly advanced along the trajectory to a location within the skull; and an aneurysm treatment device carried by the probe and dimensioned to permit the aneurysm treatment device to be introduced through the opening, at least a distal portion of the aneurysm treatment device being releasable, to grasp about the aneurysm, while a proximal portion of the aneurysm treatment device is disposed within the probe, and the probe is guided along the trajectory and the trajectory is fixed with respect to the subject's skull, wherein the distal portion of the aneurysm treatment device is released via axial translation of at least a portion of the probe without lateral motion of the probe with respect to the trajectory guide trajectory.

45. A system including:

an elongate exovascular probe, including proximal and distal ends, the probe including a substantially uniform cylindrical outer surface that is sized and shaped to be accepted within and guided by a similarly sized and shaped lumen of a trajectory guide device, the probe also including an outer dimension that is less than about 18 millimeters to permit the probe to be introduced through a similarly-sized minimally-invasive opening in a portion of a subject's skull and exovascularly advanced to an aneurysm within the skull; and an aneurysm treatment device carried by the probe and dimensioned to permit the aneurysm treatment device to be introduced via the trajectory guide device through the opening, at least a distal portion of the aneurysm treatment device being releasable, to grasp about the aneurysm, while a proximal portion of the aneurysm treatment device is disposed within the probe and the probe is accepted within the lumen of the trajectory guide device, wherein the aneurysm treatment device includes:

a normally substantially open clip that is substantially closed when retracted into a lumen of the probe, an elongate tube shaped to extend through the lumen of the probe, a distal end of the elongate tube shaped to extend out of the distal end of the probe and around a portion of the clip to substantially close a portion of the clip around a portion of the aneurysm, and a flexible strand shaped to extend through the elongate tube, and releasably coupled to a portion of the clip.

46. The system of claim 45, further including a ring shaped to engage the distal end of the elongate tube, the ring shaped to encircle a portion of the clip to hold the clip in the substantially closed position around the portion of the aneurysm.

47. A system including:

an elongate exovascular probe, including proximal and distal ends, the probe including a substantially uniform cylindrical outer surface that is sized and shaped to be accepted within and guided by a correspondingly sized and shaped lumen of a trajectory guide device, the probe also sized and shaped to permit the probe to be introduced through an opening in a portion of a subject's skull and exovascularly advanced to an aneurysm within the skull, the probe including:

an elongate outer tube, providing the substantially uniform cylindrical outer surface of the probe, the outer tube including a longitudinal outer tube lumen an elongate inner tube, including a substantially uniform cylindrical outer surface that is sized and shaped to be accepted within and guided by the outer tube lumen, the inner tube including a longitudinal inner tube lumen; and an aneurysm treatment device carried by the probe and dimensioned to permit the aneurysm treatment device to be introduced via the trajectory guide device through the opening, at least a distal portion of the aneurysm treatment device being releasable, to grasp about the aneurysm, while a proximal portion of the aneurysm treatment device is disposed within the probe and the probe is accepted within the lumen of the trajectory guide device.

48. The system of claim 47, in which the aneurysm treatment device includes a clip that is sized and shaped to fit within the inner tube lumen, when the clip is retracted into a closed position, and wherein the clip is sized and shaped to fit about a portion of an aneurysm, when the clip is expanded into an open position.

49. The system of claim 48, in which the probe further includes a strand that is sized and shaped to extend through the inner tube lumen, and wherein the strand is releasably coupled to a portion of the clip.

50. The system of claim 49, further including a ring, the ring sized and shaped to be carried within the outer tube lumen, and sized and shaped to engage a distal end of the inner tube, and sized and shaped to encircle a portion of the clip to close and hold the clip around the portion of the aneurysm.

51. A system including:

an elongate exovascular probe, including proximal and distal ends, the probe including an outer surface that is conformally sized and shaped to be accepted within and guided by a correspondingly sized and shaped lumen of a trajectory guide device, the probe also sized and shaped to permit the probe to be introduced through an opening in a portion of a subject's skull and exovascularly advanced to an aneurysm within the skull;

an aneurysm treatment device carried by the probe and dimensioned to permit the aneurysm treatment device to be introduced via the trajectory guide device through the opening, at least a distal portion of the aneurysm treatment device being releasable, to grasp about the aneurysm, while a proximal portion of the aneurysm treatment device is disposed within the probe and the probe is accepted within the lumen of the trajectory guide device;

an entry device including:
a first securing mechanism to secure the entry device in association with the subject's skull, and
a second securing mechanism to secure an orientation of a trajectory guide portion of the entry device to define a path between the minimally-invasive opening and the aneurysm; and means for providing information upon which the orientation of the trajectory guide is determined.

52. The system of claim 51, further including a local imaging device located near the distal end of the probe.

* * * * *